US00PP23244P2

(12) United States Plant Patent
Danziger

(10) Patent No.: US PP23,244 P2
(45) Date of Patent: Dec. 4, 2012

(54) *PORTULACA* PLANT NAMED 'DPAZ16'

(50) Latin Name: *Portulaca oleracea*
Varietal Denomination: DPAZ16

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 34 days.

(21) Appl. No.: 13/068,527

(22) Filed: May 13, 2011

(51) Int. Cl.
*A01H 5/00* (2006.01)

(52) U.S. Cl. ..... Plt./471

(58) Field of Classification Search ..... Plt./471
See application file for complete search history.

*Primary Examiner* — Susan McCormick Ewoldt
(74) *Attorney, Agent, or Firm* — Cassandra Bright

(57) ABSTRACT

A new and distinct *Portulaca* cultivar named 'DPAZ16' is disclosed, characterized by large yellow flowers. The new variety has a compact, semi trailing growth habit and forms a dense plant. The new variety is a *Portulaca*, normally produced as an outdoor garden or container plant.

2 Drawing Sheets

Latin name of the genus and species: *Portulaca oleracea.*
Variety denomination: 'DPAZ16'.

BACKGROUND OF THE INVENTION

The new *Portulaca* cultivar is a product of a planned breeding program conducted by the inventor, Gavriel Danziger, in Moshav Mishmar Hashiva, Israel. The objective of the breeding program was to produce new *Portulaca* varieties for ornamental commercial applications. The cross resulting in this new variety was made during September 2008.

The seed parent is the unpatented, proprietary seedling variety referred to as *Portulaca oleracea* 'PT-8-405' The pollen parent is unknown, as the crossing resulting in 'DPAZ16' was an open pollination, with unidentifiable pollen parents. The new variety was discovered in June 2009 by the inventor in a group of seedlings resulting from the 2008 crossing, in a research greenhouse in Moshav Mishmar Hashiva, Israel.

Asexual reproduction of the new cultivar 'DPAZ16' by vegetative cuttings was first performed at a research greenhouse in Moshav Mishmar Hashiva, Israel in July 2009 and has shown that the unique features of this cultivar are stable and reproduced true to type in successive generations.

SUMMARY OF THE INVENTION

The cultivar 'DPAZ16' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPAZ16' These characteristics in combination distinguish 'DPAZ16' as a new and distinct *Portulaca* cultivar:

1. Large flowers
2. Compact and dense semi trailing habit
3. Flowers open early in the morning Plants of the new cultivar 'DPAZ16' are similar to plants of the seed parent, *Portulaca oleracea* 'PT-8-405' in most horticultural characteristics, however, plants of the new cultivar 'DPAZ16' have a more dense plant habit, and larger flowers. Additionally, the new cultivar has more leaves than the seed parent.

COMMERCIAL COMPARISON

Plants of the new cultivar 'DPAZ16' are comparable to the commercial variety *Portulaca* 'Summer Joy Yellow' U.S. Plant Pat. No. 12,256. These *Portulaca* varieties are similar in most horticultural characteristics, including flower color and flower form. The new variety 'DPAZ16' differs in having somewhat smaller flowers, of a solid yellow, whereas 'Summer Joy Yellow' has a characteristic orange ring in the flower color. Additionally, 'DPAZ16' has larger leaves, a different angle of attachment of the flowers and a more compact plant habit than 'Summer Joy Yellow'.

BRIEF DESCRIPTION OF THE PHOTOGRAPHS

Figure 1:
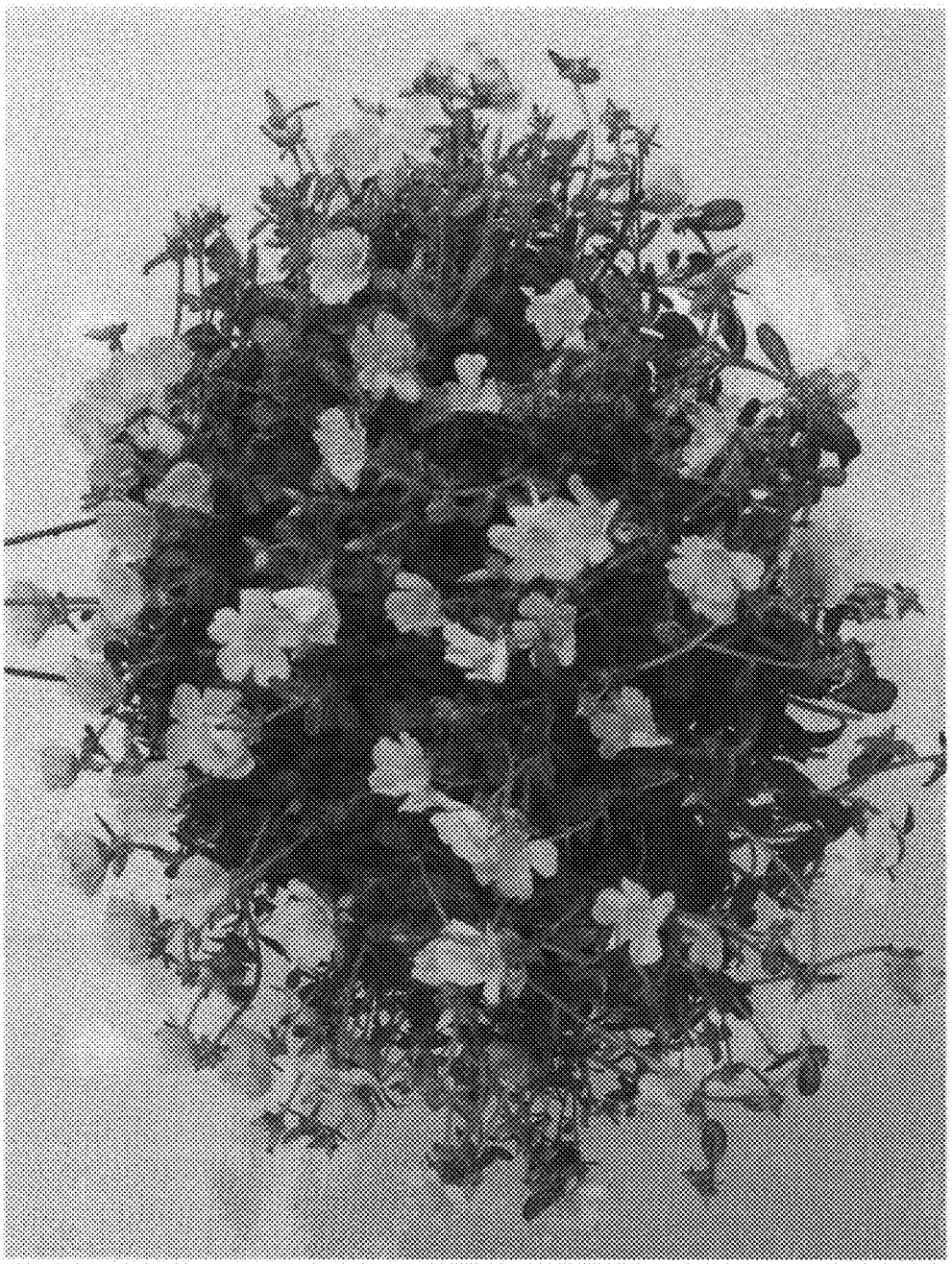

The accompanying photograph in FIG. 1 illustrates in full color a typical plant of 'DPAZ16' grown in a greenhouse, in a 13 cm basket. Age of the plant photographed is approximately 85 days from a rooted cutting.

Figure 2:
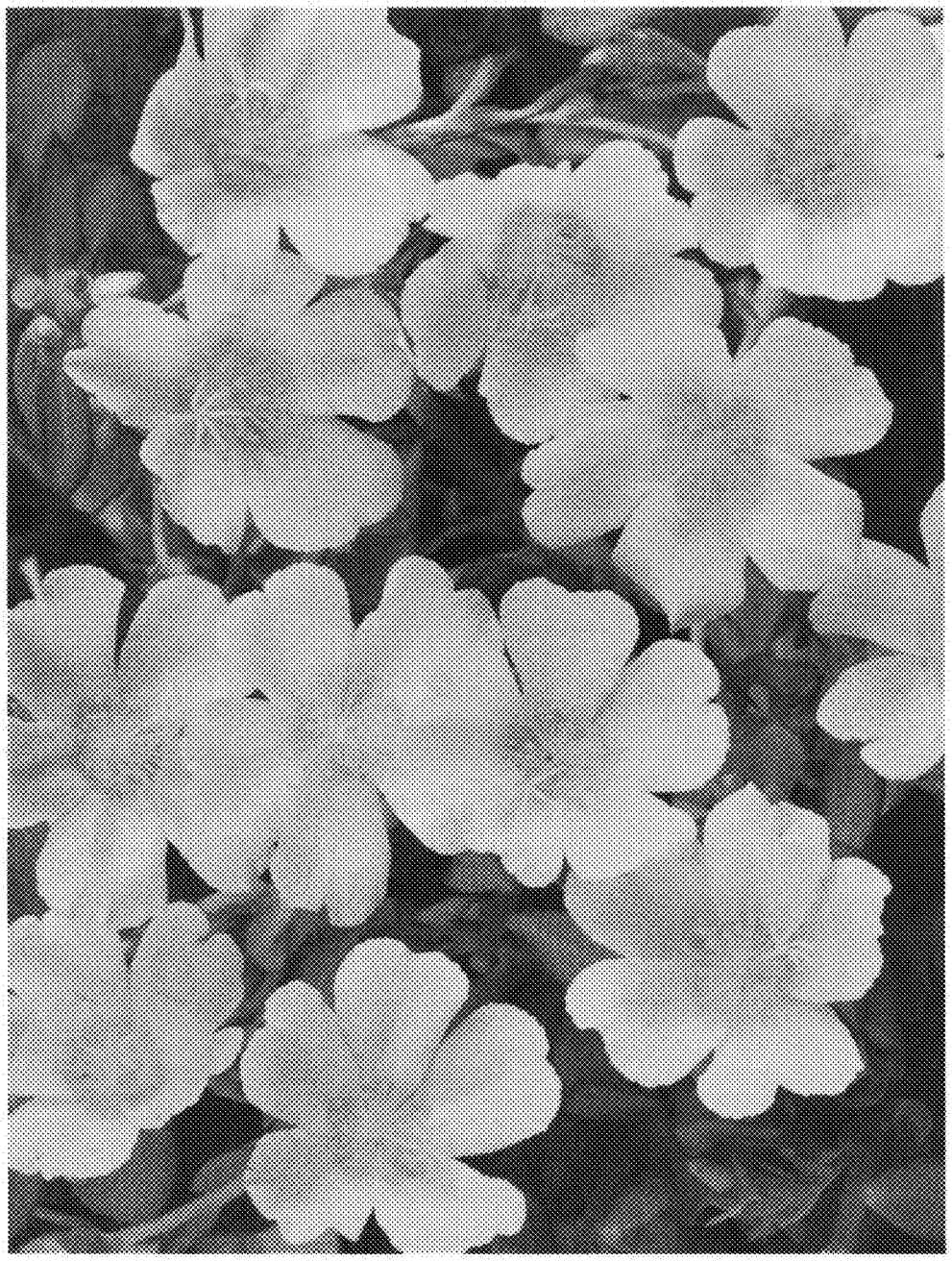

FIG. 2 illustrates in full color a close up of a typical bloom of 'DPAZ16'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DPAZ16' plants grown in a greenhouse during Spring in Gilroy, Calif. The growing temperature ranged from 14° C. to 30° C. during the day and from 10° C. to 23° C. during the night. General light conditions are bright, normal sunlight. Measurements and numerical values represent averages of typical plant types.

Botanical classification: *Portulaca oleracea* 'DPAZ16'.

PROPAGATION

Time to initiate roots: 10 to 14 days at approximately 18-21° C.
Root description: Fibrous, spreading and dense.

PLANT

Growth habit: Vigorous, semi-trailing.
Pot size of plant described: 13 cm.
Age of the plant described: 80 days.
Height: From soil level to top of the plant is 10 cm.
Plant spread: About 25-30 cm.
Growth rate: Vigor.
Branching characteristics: Free and dense basal branching. Approximately 6 main branches and 14 secondary branches.
Length of primary lateral branches: Approximately 32 cm.
Diameter of lateral branches: Approximately 0.5 cm.
Quantity of primary lateral branches: Approximately 14.
Characteristics of primary lateral branches:
*Form*.—Rounded, fleshy with ridges.
*Diameter*.—Approximately 0.5 cm.
*Color*.—At the base RHS Yellow-Green 144B with venation of RHS Greyed-Purple 187C, top RHS Yellow-Green 144B.
*Texture*.—Succulent — smooth, glabrous.
*Strength*.—Moderate.
Internode length: About 3.5 cm.

FOLIAGE

Leaf:
*Arrangement*.—Alternate.
*Quantity*.—Approximately 12 per branch.
*Average length*.—Approximately 3 cm.
*Average width*.—1.75 cm.
*Shape of blade*.—Obovate.
*Apex*.—Rounded.
*Base*.—Attenuate.
*Margin*.—Entire.
*Texture of top surface*.—Glabrous, smooth.
*Pubescence*.—None.
*Attachment angle*.—At right angle or obtuse angle to stem.
*Color*.—Young foliage upper side: RHS Green 137 A. Young foliage under side: RHS Green 137 C. Mature foliage upper side: RHS Green 137 B. Mature foliage under side: RHS Yellow-Green 147 C.
*Venation*.—Type: Pinnate. Venation color upper side: RHS Green 137B. Venation color under side: Near RHS Yellow-Green 147C. Venation color is indistinguishable from foliage.
*Petiole*.—Length: 0.25 cm. Diameter: 0.2 cm. Color: RHS Yellow-Green 144C. Texture: Glabrous.

FLOWER

Natural flowering season: From Spring to Autumn.
Days to flowering from rooted cutting: Approximately 8 weeks.
Inflorescence and flower type and habit: Terminal, single, sessile. Flower habit horizontal.
Rate of flower opening: 7 to 10 days from bud to fully opened flower.
Flower longevity on plant: Approximately 1 day.
Persistent or self-cleaning: Self-Cleaning.
Bud:
*Shape*.—Ovate with a pointed tip.
*Length*.—Approximately 1.1 cm.
*Diameter*.—Approximately 0.7 cm.
*Color*.—RHS Green 143C and edges color RHS Red-Purple 59B.
Flower size:
*Diameter*.—Approximately 4.5 cm.
Corolla/petals:
*Arrangement*.—Single flower with five distinct overlapping petals, not persistent.
*Length*.—Approximately 2.1 cm.
*Width*.—Approximately 1.7 cm.
*Quantity*.—5 Petals.
*Texture*.—Glabrous.
*Apex*.—Emarginate.
*Shape*.—Obovate.
*Margin*.—Entire.
Color:
*When opening*.—Upper surface: RHS Yellow 9A. Lower surface: RHS Yellow 6C.
*Fully opened*.—Upper surface: RHS Yellow 9A. Lower surface: RHS Yellow 6B.
Calyx/sepals:
*Quantity per flower*.—2.
*Shape*.—Deltoid.
*Length*.—Approximately 0.7 cm.
*Width*.—Approximately 0.6 cm.
*Apex*.—Acute.
*Base*.—Fused.
*Margin*.—Entire.
*Texture*.—Glabrous.
*Color*.—Upper and Lower Surface: RHS Green 143C with venations of RHS 143A and edges color RHS Red-Purple 59B.
Peduncle: None.
Fragrance: None.

REPRODUCTIVE ORGANS

Stamens:
*Number*.—About 70.
*Filament length*.—Approximately 0.6 cm.
Anthers:
*Shape*.—Oval, bilobed.
*Length*.—Approximately 0.8 mm.
*Color*.—Near RHS Yellow 9A.
*Pollen*.—Color: Near RHS Yellow-Orange 23A, but darker. Quantity: Abundant.
Pistil:
*Number*.—1 per flower.
*Length*.—Approximately 1.2 cm.
*Style*.—Length: Approximately 1 cm. Color: Near RHS Green-Yellow 1A.
*Stigma*.—Shape: Six-branched. Color: Near RHS Green-Yellow 1B. Ovary Color: Near RHS Yellow-Green 144B.

OTHER CHARACTERISTICS

Seeds and fruits: Fruits are egg-shaped 4-5 mm long with a conical shape top. Seeds are glossy black with a circular shape.
Disease/pest resistance: Neither resistance nor susceptibility to diseases or insects has been observed.
Temperature tolerance: Will not tolerate temperatures below 7° C.

What is claimed is:

1. A new and distinct cultivar of *Portulaca* plant named 'DPAZ16' as herein illustrated and described.

* * * * *